US007303530B2

(12) United States Patent
Barnes et al.

(10) Patent No.: US 7,303,530 B2
(45) Date of Patent: Dec. 4, 2007

(54) TRANSDUCER ARRAYS WITH AN INTEGRATED SENSOR AND METHODS OF USE

(75) Inventors: Stephen R. Barnes, Bellevue, WA (US); Mirsaid Bolorforosh, Portola Valley, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 472 days.

(21) Appl. No.: 10/443,257

(22) Filed: May 22, 2003

(65) Prior Publication Data

US 2004/0236223 A1 Nov. 25, 2004

(51) Int. Cl.
*A61B 8/14* (2006.01)

(52) U.S. Cl. .................................................... 600/459

(58) Field of Classification Search ........ 600/437–472; 73/570–579, 625, 626, 597; 374/100, 117; 601/2, 3; 367/7, 11, 130, 138; 29/25.35; 310/330–334

See application file for complete search history.

(56) References Cited

U.S. PATENT DOCUMENTS 4,794,384 A 12/1988 Jackson
5,158,087 A * 10/1992 Gatzke ....................... 600/459
5,560,362 A * 10/1996 Sliwa et al. ................ 600/439
5,585,546 A 12/1996 Gururaja et al.
5,606,974 A * 3/1997 Castellano et al. ......... 600/462
5,679,888 A * 10/1997 Tohda et al. .................. 73/105
5,853,005 A * 12/1998 Scanlon ...................... 600/459
6,122,338 A 9/2000 Yamauchi
6,122,538 A 9/2000 Sliwa, Jr. et al.
6,201,900 B1 3/2001 Hossack et al.
6,246,482 B1 6/2001 Kinrot et al.
6,330,057 B1 12/2001 Lederer et al.
6,338,716 B1 1/2002 Hossack et al.
6,368,275 B1 * 4/2002 Sliwa et al. ................ 600/437
6,426,582 B1 7/2002 Niederer et al.
6,461,299 B1 10/2002 Hossack
6,511,427 B1 1/2003 Sliwa, Jr. et al.
6,514,214 B2 * 2/2003 Kokate et al. .............. 600/549
6,558,330 B1 5/2003 Ayter et al.
6,789,426 B2 * 9/2004 Yaralioglu et al. ............ 73/597
2002/0009015 A1 * 1/2002 Laugharn et al. ........... 366/108
2004/0002655 A1 * 1/2004 Bolorforosh et al. ....... 600/459

OTHER PUBLICATIONS

"Studies in Optical Tomography," by X.C. Yang and B.K.P. Horn; Massachusetts Institute of Technology; latest date May 6, 2003.
"3-D Image Reconstruction in Optical Tomography," by Xiaochun Yang and Berthold K. P. Horn; latest date—Apr. 23, 2003.

(Continued)

*Primary Examiner*—Ali Imam

(57) ABSTRACT

Methods and systems for obtaining ultrasound and sensing other patient characteristics are provided from summary. One or more sensors are provided in a same transducer probe as an array of elements. For example, sensors are formed on a same semiconductor substrate, such as a silicon substrate, as microelectromechanical devices or a capacitive membrane ultrasonic transducer (CMUT). As another example, a sensor is provided separate from or attached to transducer materials. Possible sensors include temperature, pressure, microphone, chemical and/or other sensors.

10 Claims, 1 Drawing Sheet

18
12
10
14
16
20
22

OTHER PUBLICATIONS

"Optical Tomography," Project funded by Action Research Project No. A/P/0503; dated Apr. 24, 2003.

"Biosensors: A Survey Report," by Saraju P. Mohanty; Department of Comp. Sc. and Engg. at the University of South Florida, Tampa; dated Nov. 24, 2001.

"Analytical Aspects of Biosensors," by J.E. Pearson, A. Gill, and P. Vadgama; From the Section of Clinical Biochemistry, The University of Manchester; Review Article; Ann Clin. Biochem 2000; 37:119-145; dated Aug. 12, 1999.

* cited by examiner

TRANSDUCER ARRAYS WITH AN INTEGRATED SENSOR AND METHODS OF USE

BACKGROUND

The present invention relates to ultrasonic transducers, and in particular to ultrasonic transducer probes with additional functionality.

Ultrasound transducers convert between electrical and acoustic energies for imaging a patient or region of interest. Transducer elements are typically piezoelectric materials. A one or two-dimensional array of elements of piezoelectric ceramic or composite materials convert between acoustic and electrical energies. More recently, capacitive membrane ultrasonic transducers have been made. Using CMOS or other similar techniques, a flexible membrane structure is micro-machined on silicon or other semiconductor. By placing an electrode on each side of a gap defining the membrane, the transducer converts between electrical and acoustical energies.

An array of transducer elements are housed within a probe housing. For example, a housing is adapted to be held by a user and placed adjacent to the skin on an external surface of the patient. Other examples include catheter, endoscope, transesophageal and vaginal probe housings.

Other devices have been placed within a probe housing in addition to the transducer elements. For example, a transesophageal probe includes a separate tube with a thermister positioned inside the tube. As another example, U.S. Pat. Nos. 6,511,427 and 6,338,716 disclose position and orientation sensors within a housing. Using magnetic coils, the orientation and movement of a transducer housing is determined. As yet another example, U.S. Pat. Nos. 6,795,374 and 6,461,299 disclose using a membrane of a CMUT transducer to also sense pressure, such as for altering a bias voltage applied to the membrane.

BRIEF SUMMARY

The present invention is defined by the following claims, and nothing in this section should be taken as a limitation on those claims. By way of introduction, the preferred embodiments describe below include methods and systems for obtaining ultrasound information and sensing other patient characteristics. One or more sensors are provided in a same transducer probe as an array of elements. In one embodiment, sensors are formed on a same semiconductor substrate, such as a silicon substrate, as microelectromechanical devices or a capacitive membrane ultrasonic transducer (CMUT). In other embodiments, a sensor is provided separate from or attached to transducer materials. Possible sensors include temperature, pressure, microphone, chemical and/or other sensors.

In a first aspect, a transducer probe for ultrasound detection is provided. A probe housing is adapted for handheld use externally to a subject. A piezoelectric transducer element is connected with the probe housing. A sensor is exposed on an exterior surface of the probe housing.

In a second aspect, a transducer probe for ultrasound detection is provided. At least one transducer element connects with a probe housing. The transducer element is on or within a substrate. A temperature sensor is also integrated on or within the substrate.

In a third aspect, a method for obtaining multiple types of information including ultrasound information is provided. A transducer element is used to obtain the ultrasound information. A pressure sensor on or within the probe housing senses a pressure. Breath sound or tissue stiffness information about an object spaced from the probe housing is determined as a function of the pressure. For example, the stiffness of tissue spaced from the probe housing is determined as a function of the ultrasound information and the pressure. As another example, breath sounds or cardiac heart sounds are determined as a function of the pressure. As yet another example, blood pressure for a vessel spaced from the probe housing is determined as a function of the pressure.

In a fourth aspect, a transducer probe for ultrasound detection includes a probe housing. At least one transducer element connects with the probe housing, and a chemical sensor also connects with the probe housing on a surface to be exposed to fluids or tissues of a subject.

In a fifth aspect, a method for obtaining multiple types of information including ultrasound information is provided. Ultrasound information is obtained with capacitive membrane ultrasound transducer element on or within a probe housing. A pressure is sensed with a pressure sensor on or within the probe housing. Blood pressure information is determined as a function of the pressure.

In a sixth aspect, a catheter with a CMUT transducer and pressure sensor is provided.

In a seventh aspect, a transducer probe is provided for ultrasound detection. A probe housing connects with at least one transducer element on or within a substrate. A position sensor is integrated on or within the substrate.

Further aspects and advantages of the invention are described below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

To enhance the safety and/or performance of an ultrasonic system, such as providing biophysical data from the patient, sensors are integrated with ultrasound transducers. For example, CMUTs are made of micro-machined silicon. The same micro machining techniques or integrated circuit techniques are used to form other sensors, such as temperature, pressure or chemical sensors. The sensors are implemented on the same substrate as the CMUT or the CMUT membrane can function both as an ultrasound transducer and a sensor of other information.

Figure 1:
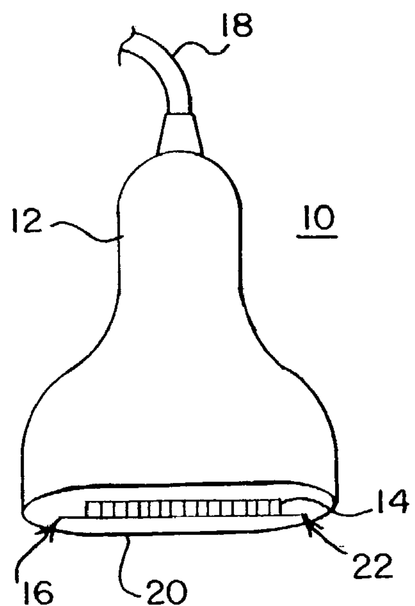
FIG. 1 is a graphical representation of a cross-sectional view of a transducer probe adapted for handheld use external to a body.

FIG. 1 shows a transducer probe 10 for ultrasound detection as a partial cross-sectional view. The transducer probe 10 includes a probe housing 12, at least one transducer element 14 and a sensor 16. Additional, different or fewer components may be provided. The transducer probe 10 connects through a cable 18 with an ultrasound imaging system for generating medical diagnostic images. The cable 18 passes information from the sensor 16 as well as the ultrasound information. The ultrasound information and sensor information are used to detect various characteristics of the signals and generate an ultrasound image or provide diagnostic information.

The probe housing 12 comprises plastic, metal, fiberglass, ceramic, resin, polymer, rubber, silicon, combinations thereof or other now known or later developed materials for housing the array of transducer elements 14. The probe housing 12 includes an acoustic window 20. The acoustic window 20 is glass, plastic, polymer, rubber, or other acoustically transparent material. The acoustic window comprises the same or different material as the rest of the probe housing 12. The acoustic window 20 is a focusing lens in one embodiment, but may provide no or minimal focusing in other embodiments. As yet another alternative, the acoustic window 20 comprises an opening or aperture free of additional material, exposing the elements 14. The transducer elements 14 are positioned adjacent to or against the acoustic window 20 for transmitting acoustic energy to and receiving acoustic energy from the patient or other subject of interest.

In the embodiment shown in FIG. 1, the probe housing 10 is shaped or adapted for handheld use externally to a subject. For example, the probe housing 12 has a generally circular or oblong cross-section for gripping by user. Alternatively or additionally, a grip or other device is provided for grasping and holding the probe housing 12. The acoustic window 20 and a lower surface 22 of the probe housing 12 intended for contact with the skin of a patient are generally flat or rounded to allow movement along the skin of the patient and prevent patient discomfort.

Figure 2:
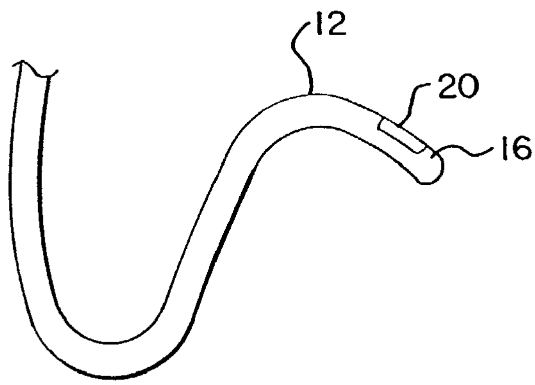
FIG. 2 is a graphical representation of a partial view of a catheter probe housing.

Alternatively, the probe housing 12 is adapted for use within or internally to a patient or subject. FIG. 2 shows a probe housing 12 for use as a catheter. The probe housing 12 is long and thin, such as 10 mm or less in circumference, to allow insertion of at least a portion of the probe housing within a circulatory system of a patient. Other transducer probes and associated housings 12 for use internal to a patient include transesophageal probes, endocavity probes and vaginal probes. The probe housing 12 is of any of various shapes adapted for comfortable or optimal use within the patient.

The one or more transducer elements 14 are piezoelectric or CMUT transducers. In one embodiment, an array of transducer elements 14 are provided and arranged in one of various configurations, such as linear, curved linear, 1.5 dimensional, 2-dimensional or combinations thereof. The transducer elements 14 connect with the probe housing 12 adjacent to the acoustic window 20. The transducer elements 14 are positioned to allow transmission and reception of acoustic energy within the patient or subject. In one embodiment, the transducer elements 14 are connected with a flexible circuit and an acoustic backing block in a transducer stack which is mounted within the probe housing 12. The backing block or stack comprises a substrate for mounting piezoelectric transducer elements. Alternatively, the transducer elements 14 are formed on a semiconductor substrate that is mounted within the probe housing 12.

Piezoelectric transducer elements 14 comprise piezoelectric, such as PZT, or other ceramics for converting between electrical and acoustical energies. Ceramic composites of PZT and polymer may also be used. Each element is defined by a kerf, electrode pattern or other configuration.

In one embodiment, one or more of the transducer elements 14 is a CMUT. CMUT includes any kind of medical ultrasound vibrating acoustic wave transmitters or receivers with one or more electrostatically charged membranes whose motion is primarily responsive to electrostatic (coulomb) forces or whose motion results in modulation of the electrostatic potential. Such electrostatic transducers include micro-machined, micro-molded, or bonded membrane systems used as a transducer. For example, CMUT includes a micro-machined ultrasound transducer utilizing electrically drivable vibrating micro-diaphragms or membranes made using micro-machining techniques, such as CMOS techniques. A capacitor electrode is provided on each side of a dielectric gap chamber. Example embodiments of CMUT transducers are shown in U.S. Pat. Nos. 6,504,795 and 6,426,582, the disclosures of which are incorporated herein by reference. The CMUTs are formed on a semiconductor substrate, such as silicon, but other semiconductor substrates may be used.

Figure 3:
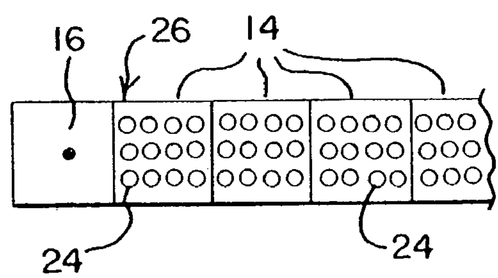
FIG. 3 is a top view of a linear array of a CMUT transducer.

FIG. 3 shows part of a linear array of transducer elements 14. Each transducer element 14 includes a plurality of doped silicon membranes 24 configured electrically to act as electrodes. The silicon membranes 24 are formed on a silicon substrate 26. The silicon substrate 26 includes doped silicon sections associated with each of the membranes 24. The doped silicon membrane 24 and doped silicon substrate act as two electrodes separated by a gap filled with fluid, gas, or vacuum. In alternative embodiments, metal or other electrically conductive material is deposited, etched or otherwise formed on the membrane or within the gap to form two capacitive plates. The dimension of the diaphragms or membranes may be in the 50 micron range, but may be smaller or larger. Multiple layers of membranes may be provided, such as disclosed in U.S. Pat. No. 6,558,330, the disclosure of which is incorporated herein by reference. Other CMUT devices that may be used are disclosed in U.S. Pat. No. 6,795,374, the disclosure of which is incorporated herein by reference. The membranes 24, doped substrate or electrodes of each element 14 are interconnected to receive or provide a common electrical signal. A single membrane 24 may be used for a single element 14 in other embodiments.

The sensor 16 is a temperature sensor, pressure sensor, microphone, chemical sensor, viscosity sensor, gas sensor or other sensor now known or later developed for sensing non-ultrasound information. The sensor 16 comprises a microelectromechanical device, an integrated circuit device, discrete analog component, digital component, combinations thereof or other sensor device now known or later developed.

The sensor 16 is exposed on a surface of the probe housing 12, such as the surface 22 of the probe 10 adapted for use against or in contact with the patient. By positioning the sensor 16 on the surface 22, the sensor 16 is placed on or near the skin of the patient during use. For the catheter embodiment shown in FIG. 2, the sensor 16 is exposed on the surface of the probe housing 12 near the acoustic window 20. In alternative embodiments, the sensor 16 is positioned within the probe housing 12 rather than being exposed on a surface of the probe housing 12. In yet other alternative embodiments, the sensor 16 is positioned on or near the transducer elements 14 and/or the acoustic window 20. While one sensor 16 is shown, multiple sensors in similar or different locations may be provided on a single probe housing 12.

In one embodiment, the sensor 16 comprises a temperature sensor connected with a probe housing 12 adjacent to the acoustic window 20 and on a same side surface 22 of the probe housing 12 as the acoustic window 20. Where the temperature sensor 16 is positioned within the probe housing 12, a temperature of the probe housing or transducer elements 14 is measured. Transducer probes 10 must be maintained at a temperature that prevents injury to a patient. By monitoring a temperature of the transducer probe 10, various characteristics of operation of the transducer probe may be altered to avoid patient injury. For example, the amplitude of transmitted ultrasonic waves may be decreased, the pulse repetition frequency or other transmit characteristic may be altered to reduce the temperature. Alternatively, a temperature warning signal is provided to the user to indicate excessive transducer probe temperatures.

In an alternative embodiment, the temperature sensor 16 senses the temperature of the patient or subject being examined for patient safety or for patient diagnostic information. The patient's skin, blood or interior tissue is sensed by the temperature sensor 16. For sensing tissue or fluids, the temperature sensor 16 is exposed on an outer surface of the transducer probe 12, but may be displaced from the outer surface for remote temperature sensing, such as by an infrared temperature sensor.

In one embodiment, the temperature sensor 16 is integrated on or within a substrate, such as a backing block of a piezoelectric transducer or a semiconductor substrate of a CMUT transducer. The temperature sensor 16 is integrated on a same substrate as the transducer elements 14. Alternatively, a different substrate is used. In one embodiment, the temperature 16 is a microelectromechanical device formed on a semiconductor substrate, such as formed with a CMUT transducer. For example, a bimetal structure or other structure that flexes or moves as a function of temperature generates different electrostatic or capacitive characteristics as a function of temperature. Using electrodes formed on a microelectromechanical structure, the electrostatic forces are sensed to determine temperature. None, part or all of the circuitry for sensing the forces are integrated on the substrate with the microelectromechanical device. In alternative embodiments, the temperature sensor 16 comprises a diode, transistor, thermister, combinations thereof or other now known or later developed devices for sensing temperature. For example, a diode or transistor connects as an input to a differential amplifier connected with a reference voltage. Changes in voltage response of the transistor or diode indicate changes in temperature. The output of the differential amplifier indicates a change in temperature. The temperature sensing diode, transistor, differential amplifier or other circuitry is in part or entirely integrated on a same semiconductor substrate as each other and/or the element 14, but the integrated circuit components may be on a different substrate in other embodiments. Using microelectromechanical temperature sensors or integrated circuit temperature sensors on a same substrate as the transducer elements 14, the temperature sensor 16 is positioned between transducer elements 14 in one embodiment, but may be positioned adjacent to, at an edge of the transducer elements 14 as shown in FIG. 3 or spaced from the elements 14. With the temperature sensor 16 integrated on a same substrate with the CMUT transducer elements 14, CMOS or other CMUT-compatible processes are used for forming the temperature sensor. Different processes may be used in alternative embodiments.

In another embodiment of the sensor 16, the sensor 16 is a pressure sensor. For example, embodiments described in U.S. Pat. No. 6,461,299, filed Dec. 22, 1999, disclosure of which is incorporated herein by reference, are included with a CMUT or piezoelectric transducer array. A membrane or other capacitive element flexes or moves as a function of pressure applied to the element. The change in capacitance or capacitance is measured to detect a pressure. In alternative embodiments, a strain gauge or other analog or digital circuit is used for detecting pressure. Where a microelectromechanical device, such as a membrane, or integrated circuit is used for the pressure sensor 16, the pressure 16 sensor is integrated in part or entirely on the same semiconductor substrate as CMUT transducer. In alternative embodiments, separate substrates are used for part or all of the pressure sensor. Where the membranes 24 of CMUT transducers have sufficient range or sensitivity to avoid bottoming out or undesirable operation, the same membrane 24 used for transducing between acoustic and electric energies is used as a pressure sensor as well. A DC offset due to pressure or low frequency variation due to pressure is measured as well as higher ultrasound frequency capacitance effects. In alternative embodiments, a pressure sensing membrane manufactured with the same technology, such as CMOS processing, is formed on the same substrate but with different membrane characteristics than membranes for a CMUT transducer elements 14. For example, a pressure sensor membrane is less stiff by being thinner and/or being less tense than a membrane being used for transducing ultrasound and electrical energies.

In one embodiment, the pressure sensor 16 is adapted as a microphone operable to receive acoustic energy other than ultrasound frequencies, such as acoustic sounds associated with breathing or the heart cycle. Such a microphone has membrane or other sensory characteristics adapted to receive acoustic energy at select frequencies (e.g. low frequencies as compared to ultrasound) and may optionally filter out acoustic energy at other frequencies.

The pressure sensor 16 is positioned on a same surface 22 of the probe housing 12 for contact with the skin of a subject. None, one or more layers of flexible material may be provided between the pressure sensor 16 and the skin of the subject. In one embodiment, the pressure sensor 16 is positioned adjacent to the array of elements 14, but may be positioned between elements 14 or on or adjacent to the acoustic window 20. In the catheter embodiment of FIG. 2, the pressure sensor 16 is positioned on a same side of the catheter as the acoustic window 20 or the transducer elements 14, but may be positioned on different sides or within a port as part of the same or separate substrate as the transducer elements.

In other embodiments, the sensor 16 is a chemical sensor. A chemical surface, integrated circuit structure, microelectromechanical structure, optical sensor or other device responsive to chemical characteristics, such as a chemical type, blood gas level, pH level, existence of a particular chemical, amount of a particular chemical or other chemical characteristics is used. For example, a chemical or biological recognition element with or without a permeable membrane and a signal transducer element (e.g., electrochemical (amperometry or potentiometry), electrical (ion-sensitive field effect transistor, conductance, impedance, potential, or current), optical (luminescence, fluorescence or refractive index), thermal and/or piezoelectric) are provided to determine a chemical characteristic. An amplification or processing element may be integrated with the analyte responsive recognition element and/or the signal transducer element. Using membrane entrapment, physical adsorption, matrix entrapment, reaction chamber, covalent bonding or other physical structure for exposure, a biological recognition phase (enzyme, antibody, receptor, DNA or other chemical)

interacts with the analyte of interest to produce a charge or optical change at the sensor-transducer interface or electrode. Any now known or later developed chemical sensors, such as immunosensors, optrodes, chemical canaries, resonant mirrors, glucometers, biochips, and/or biocomputers, may be used.

In one embodiment, the chemical sensor 16 is integrated on a same substrate, such as a silicon substrate, as the transducer elements 14. CMOS, micromachining, bonding, deposition, masking, etching or other processes are used to form the chemical sensor 16 on the same substrate. An electrical or other output of the chemical sensor 16 is measured to determine the characteristic of a desired chemical. The chemical sensor 16 connects with the probe housing 12 on a surface exposed to fluids or tissues of the subject, such as on a tip portion of a catheter of FIG. 2 or on a surface 22 for contact with the skin of a patient. In the catheter or other endocavity embodiment, the chemical sensor may be positioned within a port or cavity on the probe housing 12. In some embodiments, the chemical sensor 16 is in direct contact with the tissue or fluid to be sensed.

To avoid deterioration or undesired performance of the transducer elements, such as CMUT elements on a same substrate, the transducer elements 14 are encapsulated by a blood or other fluid impervious barrier and the chemical sensor 16 is free of the fluid impervious barrier. For example, any of various coverings or other physical structures are deposited using CMOS processes as disclosed in U.S. Pat. No. 6,426,582, to avoid fluid damage to the performance of the transducer element 16. The same covering is etched from or not deposited on the chemical sensor 16 positioned on the same substrate. By using semiconductor substrate based chemical sensors, the chemical sensor 16 is small and inexpensive, so it may be easily provided with the transducer probe 10.

In methods of operation of the transducer probe 10, the transducer elements 14 are used to obtain ultrasound information. For example, electrical energy is applied to the transducer elements 14 and converted to acoustic energy. The acoustic energy propagates from the elements 14 into the patient. The acoustic energy reflects off of tissue barriers or other structures or fluids within the patient and returns, in part, to the elements 14. In response to the ultrasound pressures applied to the elements 14, the elements 14 generate electrical energy representing the echo signals. For example, acoustic energy impinging on a CMUT transducer causes the membrane to vibrate. Capacitive or electrostatic forces are created in response to variations of the membrane or the distance between electrodes associated with the membrane gap. As an example for piezoelectric elements, the acoustic energy causes compression or expansion of the crystalline or ceramic structure of the piezoelectric material to generate electrical energy on opposing electrodes. The same or different transducer elements 14 are used for transmissions and reception.

In one embodiment, the temperature of a component of the transducer probe 10 or of the subject being examined is sensed. A temperature value is then recorded or provided to the user on a display on the transducer probe 10 or on the ultrasound system. Alternatively, the temperature is used to control operation of the ultrasound system or ultrasound probe 10. In yet another alternative embodiment, acquired ultrasound information is adjusted or altered as a function of temperature, such as to account for differences in performance of the tissue structure being examined or the ultrasound transducer elements 14 as a function of temperature. The temperature values provide diagnostic information or adjust operation of the ultrasound system.

Figure 4:
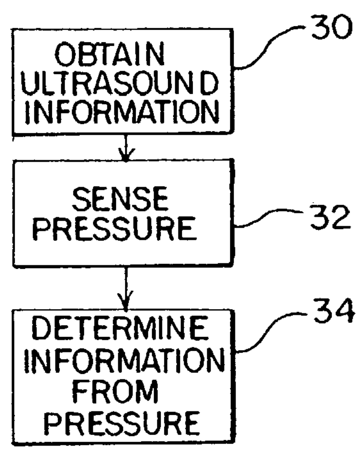
FIG. 4 is a flow chart diagram of one embodiment for determining information from a pressure sensor.

FIG. 4 shows one embodiment of a method for using sensed pressure information in addition to or other than ultrasound pressures. In act 30, ultrasound information is obtained as discussed above.

In act 32, a pressure is sensed with a pressure sensor on or within the probe housing 12. The sensed pressure is a pressure other than an ultrasound pressure, such as an acoustic pressure having a greater or lesser frequency. Either characteristics of the pressure sensor or a filter applied to pressure sensed signals isolates the desired pressure information. In one embodiment, the pressure is sensed with a pressure sensor on a same substrate as a CMUT transducer element, such as using the CMUT transducer element to sense a nonultrasound pressure. As an alternative embodiment, the pressure is sensed with a pressure sensor separate from a piezoelectric transducer element and any other piezoelectric elements for obtaining ultrasound information, such as being provided on separate substrates or at a location spaced away from the transducer elements 14. The sensed pressure information is amplified and provided to an ultrasound system or otherwise converted to diagnostic pressure information.

In act 34, information about an object spaced from the probe housing 12 is determined as a function of the pressure information. Alternatively, the pressure representing a force being applied to the pressure sensor or probe housing 12 is measured. Where the pressure information is associated with breathing sounds or cardiac heart sounds of vessel or lung tissues spaced from the transducer array, the breathing cycle or cardiac cycle may be monitored as a function of time. The pressure information is associated with the lungs or heart spaced from the transducer array by intervening tissue or by fluid. For example, breath sound monitoring is used during application of anesthesia, such as during surgical procedures being used with ultrasound catheters or transesophageal transducers.

Blood pressure may be determined for vessels or other structures spaced away from the pressure sensor. For example, pressures radiating from pressure variations in a vessel are transmitted through a vessel wall or other intervening tissue or fluids to the pressure sensor. As another example, a probe with an integrated occluding cuff is provided. The cuff is used to collapse the vessel or apply an external pressure around an extremity. Ultrasound information, such as Doppler flow information, is used to detect flow past the occlusion. A pressure sensor on or within the probe or integrated cuff measures the occluding pressure. The pressure waveform is determined from the Doppler information and the pressure. The Doppler indicates the time that flow starts as the pressure of the cuff decreases and the time flow stops when the pressure of the cuff is greater than the cardiac pressure. A series of time and pressure data points are obtained as the cuff pressure decreases. Once the cardiac cycle pressure is greater than the cuff pressure, flow begins and is detected by the Doppler signal. The flow will end when the cardiac pressure during the cycle becomes less than the cuff pressure. The series of time and pressure data points are used to create a waveform representing cardiac pressure as a function of time. Once the flow continues even during diastolic portion of the cardiac cycle, the process ends or is repeated. By using a CMUT ultrasound transducer integrated with a pressure sensor and integrated or separate from supporting electronic circuits, an affordable blood pressure sensor is provided.

Alternatively, blood pressure of blood contacting the pressure sensor is determined. For example, a CMUT device is used in a catheter probe for obtaining ultrasound information. Either the same membranes, separate pressure sensor on the same substrate (e.g., separate membrane) or a sensor on a different substrate than the CMUT device is used to directly measure the blood pressure at one point in time or over at least a portion of a cardiac cycle. The pressure sensor has a same or different coating or protection from blood as the CMUT or transducer elements. For example, the pressure sensor is a membrane with characteristics (e.g. thickness, stiffness, diameter or size) adapted for sensing blood pressure. To sense the pressure, no or a thin coating of material is provided. The CMUT on the same substrate has a thicker coating or is isolated from the pressure sensor by a barrier, such as a deposited polymer acoustic window material. In one embodiment, the pressure sensor is exposed on an outer surface of the catheter. In alternative embodiments, the pressure sensor is exposed within a port on the catheter or is placed within the catheter to sense pressure transmitted through an outer coating or surface of the catheter.

Yet another example of determining information about an object spaced from the probe housing as a function of the measured pressure is elasticity imaging. In elasticity imaging, a stiffness of tissue structures is determined as a function of tissue deformation measured using the ultrasound information and the sensed pressure. Ultrasound information is acquired where tissue is subjected to one pressure level, such as by pressing a transducer housing 12 against a skin surface. Pressure applied by the transducer housing 12 deforms tissues. Stiff tissues deform less in response to the pressure than flexible or soft tissues. The pressure measurement acquired by the pressure sensor is used to calibrate or alter the ultrasound data to reflect the stiffness of the tissue. In one embodiment, the absolute stiffness is the pressure divided by the displacement. Alternatively or additionally, ultrasound information associated with different pressures applied to tissue structures is acquired. The difference in pressure is used to determine or calibrate the differences between the responses in the ultrasound information associated with the two different pressures. Acquiring the ultrasound information with a known pressure also allows calculation of an actual stiffness or softness of tissue based on an amount of deformation associated with two different pressures. The ultrasound image information is used to determine an amount of deformation. The stiffness of the tissue is a function of the amount of deformation and the pressure applied to cause the deformation.

Chemical characteristics of blood or other tissue is measured with a chemical sensor during ultrasound imaging. For example, blood gas level, pH or existence of a particular chemical or chemicals within the blood or other fluid is detected with a chemical sensor during imaging. For use external to a patient, chemicals on the surface of the skin or within the skin of the patient are detected during ultrasound imaging. Gas or viscosity measurements associated with substances on the skin or within a patient may also be measured.

In yet another embodiment of the transducer probe 10 of FIG. 1 or catheter probe of FIG. 2, the sensor 16 is a position sensor. The transducer elements 14 of the array of elements 14 are formed on or within a substrate. For example, the transducer elements 14 are capacitive membrane ultrasonic transducer elements formed on a semiconductor substrate. The position sensor is integrated on or within the same substrate. For example, the position sensor is formed using CMOS or other microelectromechanical processes on the same wafer of silicon or other substrate.

Any of various position sensors may be used. For example, a microelectromechanical laser gyroscope device is formed on the semiconductor substrate. As another example, an optical sensor is formed on the semiconductor substrate. Any of various optical sensors may be used, such as disclosed in U.S. Patent Publication No. 20040167402, the disclosure of which is incorporated herein by reference. The optical sensor may have the structure and/or use the methods disclosed in U.S. Pat. Nos. 4,794,384; 6,330,057; and 6,246,482, the disclosures of which are incorporated herein by reference.

In one embodiment, the optical sensor is a light source and a camera. The light source is a light emitting diode, such as a high peak power pulsed laser diode. The light source emits light at any of various wavelengths in the optical spectrum. In one embodiment, the light source emits light at a wavelength of about 700–1000 nanometers or other wavelength for passing into tissue. For example, a red LED emitting a wavelength around 700 nanometers may be used. Shorter wavelengths are more likely to reflect from the skin surface rather than pass through tissue, but may also be used. In alternative embodiments, the light source is not provided or is separate from the probe housing 12.

The camera is a complementary metal-oxide semiconductor (CMOS) sensor, such as a low-light sensitive photodetector. In alternative embodiments, a CCD, photodetector cells or other optical wavelength sensor is provided. The light source transmits light into tissue and the light reflects from or passes through the tissue onto the camera. The camera detects or senses information at least in part at the wavelength of the light source. Any of speckle, phase shifts, phasing, frequency, or other characteristics of received light may be used to detect motion.

The position sensor is positioned on, within or adjacent to the housing surface of the probe housing 12. For example, a gyroscope based position sensor is within the probe housing 12, and an optical sensor is positioned adjacent a surface of the probe housing 12. By positioning the optical sensor adjacent to an acoustic window 20, adjacent to the transducer array behind the acoustic window 20 or adjacent to an outer surface adapted for placement adjacent to or in contact with the tissue surface, the optical sensor is positioned to receive light from the tissue. In alternative embodiments, the optical sensor is positioned away from the skin surface but directed towards the skin surface for measuring movement of the probe housing 12. In yet other alternative embodiments, multiple position sensors are provided on the substrate in the probe housing 12.

In a further embodiment using an optical position sensor, a plurality of optical sensors are used with an array of ultrasound transducer elements 14. For example, an array of optical sensors is formed adjacent to the array of transducer elements 14. The array of optical sensors is of any configuration, but may be linear in one embodiment, such as in a "T" pattern, an "I" pattern, a "+" pattern or other arrangements. The linear array of optical sensors is at a non-zero angle, such as orthogonal, to a linear array of transducer elements. Other angles may be used. As another example, single optical sensors or arrays of optical sensors are positioned around the array of transducer elements. Various possible arrangements are shown in U.S. Pat. No. 6,201,900, the disclosure of which is incorporated by reference.

The optical sensors are positioned to measure movement of the probe housing 12 relative to a target. U.S. Pat. No.

6,201,900 uses multiple arrays for 3D or extended field of view image reconstruction. One transducer array is used for acquiring images. The imaging array and/or other arrays are used for tracking movement of the probe housing 12. The tracking arrays may be optical sensors or arrays of optical sensors, avoiding increased beamformer channels for tracking. By using optical sensors adapted for optical tomography or responsive to light passing within tissue, any movement in any dimension of the probe housing 12 is measured.

Optical tomography is developed for visualization of surfaced tissues, such as the skin, brain or other organ, but may also be used for tracking motion. Human tissue has a relatively transparency to infrared light in the region of 700–1000 nm. Most approaches to optical tomography operate similarly to other medical imaging modalities such as X-ray Computed Tomography (CT), Single Photon Emission Computed Tomography (SPECT), Positron Emission Tomography (PET), Electrical Impedance Tomography (EIT) or Ultrasound, but rely on detecting a characteristic of light passed through or reflected in tissue. In one approach, due to the rapid attenuation of light in tissue and the ambiguity associated with absorption as opposed to reflection of light in tissue, other processes may be used, such as time resolved photon migration. In one embodiment, a resistive circuit simulates the physics of photon migration. The distribution of photon flux is sensitive to the ratio of the absorption coefficient and the diffusion coefficient but not as sensitive to changes in the scattering and absorption that leave this ratio constant. Absorption and scattering coefficients are mapped to horizontal and grounding conductance, where the mapping is used as a statistical parameter estimation problem. Parameters are chosen to minimize the misfit of predictions from observations. For more complicated geometries, an iterative approach using finite element error analysis may be used.

In another embodiment, any of various light characteristics are used to generate a frame of data. Subsequent frames of data are compared to determine translation and/or rotation motion, such as using correlation, minimum sum of absolute differences, cross-correlation or other calculations.

In one embodiment using the motion tracking of the optical sensors, two linear or curved linear optical arrays are placed orthogonally on both edges or ends of a linear or curved linear ultrasound array. All three arrays are used for probe movement tracking, such as implemented in SeaScape imaging by Siemens Medical Solutions, USA or as described in U.S. Pat. No. 6,201,900. For example, the ultrasound transducer array tracks lateral left-right movements (X axis) and rotation (around Z axis) in the imaging plane. This is performed at the same time while imaging with this ultrasound array. Two optical sensor arrays are used for tracking probe movements out of the imaging planes. The optical sensor arrays provide tracking of transitional movement in the elevation direction (along Z axis) and two rotations (around X and Y axis) out of the imaging plane.

Using optical sensors may allow for tracking simultaneously with ultrasound imaging without a frame rate reduction. Optical sensors and a processor for tracking may be implemented using cheaper circuitry than for additional acoustic beamformers for the tracking arrays. Due to very small wavelengths of light optical arrays, the size of the optical arrays may be smaller than ultrasound arrays, avoiding or limiting an increase in size of the orthogonal arrays. Using the motion tracking with optical sensors allows for three dimensional, extended field of view and two-dimensional with warping motion compensation ultrasound imaging. Alternatively, the imaging array is also an optical array.

While the invention has been described above by reference to various embodiments, it should be understood that many changes and modifications can be made without departing from the scope of the invention. For example, multiple sensors of the same or different types of sensors may be used on a same probe housing 12. One temperature sensor may be used for measuring a probe temperature and another temperature sensor for measuring a tissue temperature. Multiple pressure sensors may be used on a same probe housing with a temperature sensor or chemical sensors. Any of various probe housing shapes, sizes or structures may be used.

It is therefore intended that the foregoing detailed description be regarded as illustrative rather than limiting, and that it be understood that it is the following claims, including all equivalents, that are intended to define the spirit and scope of this invention.

We claim:

1. A transducer probe for ultrasound detection, the transducer probe comprising:

a probe housing;

an imaging array of transducer elements connected with the probe housing, the transducer elements being on or within a substrate; and a temperature sensor integrated on or within the substrate.

2. The probe of claim 1 wherein the transducer elements comprise a capacitive membrane ultrasonic transducer and the substrate comprises a semiconductor substrate.

3. The probe of claim 2 wherein the temperature sensor comprises a microelectromechanical device formed on the semiconductor substrate.

4. The probe of claim 2 wherein the temperature sensor comprises at least in part an integrated circuit component on the semiconductor substrate.

5. The probe of claim 1 wherein the temperature sensor is integrated between at least two of the transducer elements.

6. The probe of claim 1 wherein the temperature sensor is positioned to measure a temperature of the probe housing.

7. The probe of claim 1 wherein the temperature sensor is positioned to measure a temperature of a subject being examined.

8. The probe of claim 1 wherein the temperature sensor integrated on or within the substrate comprises the temperature sensor formed on or within the substrate.

9. The probe of claim 8 wherein the temperature sensor is formed on the substrate.

10. The probe of claim 8 wherein the temperature sensor is formed within the substrate.

* * * * *